United States Patent
Oh

(10) Patent No.: US 9,924,301 B2
(45) Date of Patent: Mar. 20, 2018

(54) METHOD OF CONTROLLING DEVICE AND DEVICE THEREOF

(71) Applicant: SAMSUNG ELECTRONICS CO., LTD., Suwon-si (KR)

(72) Inventor: Ki-jeong Oh, Bucheon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 14/870,142

(22) Filed: Sep. 30, 2015

(65) Prior Publication Data

US 2016/0119743 A1    Apr. 28, 2016

(30) Foreign Application Priority Data

Oct. 22, 2014 (KR) .................. 10-2014-0143597

(51) Int. Cl.
| | |
|---|---|
| *H04W 60/00* | (2009.01) |
| *H04W 4/00* | (2018.01) |
| *H04L 12/24* | (2006.01) |
| *H04L 29/08* | (2006.01) |
| *G06F 19/00* | (2018.01) |
| *H04N 1/00* | (2006.01) |

(52) U.S. Cl.
CPC ........ *H04W 4/008* (2013.01); *G06F 19/3406* (2013.01); *H04L 41/0803* (2013.01); *H04L 67/306* (2013.01); *H04N 1/00127* (2013.01); *H04N 1/00307* (2013.01); *H04N 1/00514* (2013.01); *H04N 1/00973* (2013.01); *H04W 60/00* (2013.01); *H04L 67/125* (2013.01)

(58) Field of Classification Search
USPC ............... 455/41.2, 419, 456.1, 456.2, 66.1; 600/109, 160, 101, 445, 476, 462, 459
See application file for complete search history.

(56) References Cited

U.S. PATENT DOCUMENTS

| | | | |
|---|---|---|---|
| 9,258,493 B2 | 2/2016 | Kang | |
| 2004/0146192 A1* | 7/2004 | Langan | ................ A61B 6/4233 382/132 |
| 2009/0122149 A1* | 5/2009 | Ishii | ................... H04N 1/00127 348/222.1 |
| 2011/0215921 A1 | 9/2011 | Ben Ayed et al. | |
| 2012/0068812 A1* | 3/2012 | Yamamoto | ............... G06K 7/00 340/5.1 |

(Continued)

FOREIGN PATENT DOCUMENTS

| | | |
|---|---|---|
| KR | 10-2010-0040126 A | 4/2010 |
| KR | 10-2013-0094671 A | 8/2013 |

(Continued)

OTHER PUBLICATIONS

International Search Report dated Feb. 19, 2016 issued by the International Searching Authority in counterpart International Application No. PCT/KR2015/010622 (PCT/ISA/220/210).

(Continued)

*Primary Examiner* — Ganiyu A Hanidu

(74) *Attorney, Agent, or Firm* — Sughrue Mion, PLLC

(57) ABSTRACT

A device and a method of controlling the device are provided. The method includes detecting a mobile device within a distance from the device, receiving user configuration information from the mobile device, and performing an operation of the device based on the user configuration information.

28 Claims, 10 Drawing Sheets

(56) References Cited

U.S. PATENT DOCUMENTS

| | | | |
|---|---|---|---|
| 2013/0060480 A1* | 3/2013 | Korhonen | A61B 5/1118 702/19 |
| 2013/0094628 A1* | 4/2013 | Lalena | A61B 6/4283 378/98 |
| 2013/0217333 A1* | 8/2013 | Sprigg | H04W 4/008 455/41.2 |
| 2014/0113589 A1 | 4/2014 | Kurupacheril et al. | |
| 2014/0157390 A1 | 6/2014 | Lurey et al. | |
| 2014/0164997 A1* | 6/2014 | Lee | G06F 3/04883 715/810 |
| 2014/0370879 A1* | 12/2014 | Redding | H04W 4/001 455/419 |
| 2014/0374476 A1* | 12/2014 | Ban | G06Q 30/02 235/375 |
| 2015/0015379 A1 | 1/2015 | Yoon | |

FOREIGN PATENT DOCUMENTS

| | | |
|---|---|---|
| KR | 1020130096525 A | 8/2013 |
| WO | 2012/163408 A1 | 12/2012 |

OTHER PUBLICATIONS

Written Opinion dated Feb. 19, 2016 issued by the International Searching Authority in counterpart International Application No. PCT/KR2015/010622 (PCT/ISA/237).

Jong-Woo Hong, et al.; "Wi-Fi Direct Communication Technologies and Applications"; Information & Communications magazine; May 2013; vol. 30; No. 6; pp. 26-32.

"LG Optimus Big review"; in NAVER blog [online]; May 31, 2011; (http://hm3548.blog.me/50112593502); 4 pgs. total.

Communication dated Feb. 29, 2016 issued by the Korean Intellectual Property Office in counterpart Korean Patent Application No. 10-2014-0143597.

Communication dated Nov. 13, 2015, issued by the Korean Intellectual Property Office in counterpart Korean Application No. 10-2014-0143597.

Communication dated Jul. 27, 2016, issued by the Korean Intellectual Property Office in counterpart Korean Patent Application No. 10-2014-0143597.

Communication dated Aug. 23, 2017 issued by the European Patent Office in counterpart Application No. 15852602.0.

* cited by examiner

METHOD OF CONTROLLING DEVICE AND DEVICE THEREOF

CROSS-REFERENCE TO RELATED APPLICATION

This application claims priority from Korean Patent Application No. 10-2014-0143597, filed on Oct. 22, 2014, in the Korean Intellectual Property Office, the disclosure of which is incorporated herein in its entirety by reference.

BACKGROUND

1. Field

Apparatus and methods consistent with exemplary embodiments relate to a device and a method of controlling the device.

2. Description of the Related Art

Along with the introduction of various electronic devices, in many cases, a plurality of users may use a single device together. When a user logs onto a device, the device may be set by the user that has logged on. The device may operate under set conditions. For example, in the case of a medical imaging apparatus, a user that wants to capture a medical image may input an ID and a password to log onto the medical imaging apparatus. The medical imaging apparatus may display a user interface (e.g., an index or a tool shown on a viewer) that is set with respect to the ID that is logged in, or capture a medical image according to set imaging conditions.

However, in the example above, the user may have to inconveniently log in by inputting his or her ID and password by oneself to set the device to personally-preferred settings. Also, because pieces of configuration information of the users are stored in the device, when the users want to use another device, the users may have to newly set the other device.

SUMMARY

Exemplary embodiments may address at least the above problems and/or disadvantages and other disadvantages not described above. Also, the exemplary embodiments are not required to overcome the disadvantages described above, and an exemplary embodiment may not overcome any of the problems described above.

One or more exemplary embodiments include a device and a method of setting a device by using a mobile device.

According to an aspect of an exemplary embodiment, there is provided a method of controlling a device, the method including detecting a mobile device within a distance from the device, receiving user configuration information from the mobile device, and performing an operation of the device based on the user configuration information.

The user configuration information may include user interface information of the device, and the performing may include displaying a user interface based on the user interface information.

The method may further include determining whether the mobile device is registered to the device, and the receiving may include receiving the user configuration information from the mobile device in response to the determining that the mobile device is registered to the device.

The method may further include registering the mobile device to the device in response to the determining that the mobile device is not registered to the device.

The method may further include receiving a wireless signal from the mobile device, and the detecting may include detecting that the mobile device is within the distance from the device based on the wireless signal.

The device may include a medical imaging apparatus.

The user configuration information may include a setting value for capturing an image, and the performing may include capturing an image based on the setting value.

The method may further include transmitting, to the mobile device, information of an image.

The information of the image may include an image retake rate.

A non-transitory computer-readable storage medium may store a program including instructions configured to cause a computer to perform the method.

According to an aspect of another exemplary embodiment, there is provided a method of providing configuration information to a device, the method being performed by a mobile device, and the method including receiving a configuration information request from the device in response to the mobile device being within a distance from the device, and transmitting, to the device, user configuration information in response to the receiving the configuration information request.

The user configuration information may include user interface information of the device.

The method may further include receiving a registration request from the device, and transmitting, to the device, identification information of the mobile device in response to the receiving the registration request.

The method may further include transmitting, to the device, a communication signal.

The device may include a medical imaging apparatus.

The user configuration information may include a setting value for capturing an image.

The method may further include receiving information of an image from the device, and displaying at least one among the information of the image and statistics of the information of the image.

The information of the image may include an image retake rate.

A non-transitory computer-readable storage medium may store a program including instructions configured to cause a computer to perform the method.

According to an aspect of another exemplary embodiment, a device includes a detector configured to detect a mobile device within a distance from the device, an interface configured to receive user configuration information from the mobile device, and a controller configured to perform an operation of the device based on the user configuration information.

The device may include a medical imaging apparatus.

The user configuration information may include a setting value for capturing an image, and the controller may be configured to control the device to capture an image based on the setting value.

The interface may be further configured to transmit, to the mobile device, information of an image.

The controller may be further configured to determine whether the mobile device is registered to the device, and the interface may be further configured to transmit, to the mobile device, a registration request in response to the controller determining that the mobile device is not registered in the device, and receive identification information of the mobile device from the mobile device.

The detector may be further configured to detect another mobile device within the distance from the device, the controller may be further configured to determine whether to change from the mobile device to the other mobile device based on at least one among a grade of each of the mobile device and the other mobile device and an input selection of the other mobile device, and the communicator may be further configured to receive user configuration information from the other mobile device in response to the controller determining to change from the mobile device to the other mobile device.

The communicator may be further configured to transmit, to the mobile device, a configuration information request for the user configuration information.

According to an aspect of another exemplary embodiment, a mobile device includes a communicator configured to receive a configuration information request from a device in response to the mobile device being within a distance from the device, and a controller configured to control the communicator to transmit, to the device, user configuration information in response to the communicator receiving the configuration information request.

The device may include a medical imaging apparatus.

The user configuration information may include a setting value for capturing an image.

The mobile device may further include a display, the communicator may be further configured to receive information of an image from the device, and the controller may be further configured to control the display to display at least one among the information of the image and statistics of the information of the image.

BRIEF DESCRIPTION OF THE DRAWINGS

The above and/or other aspects will become more apparent by describing exemplary embodiments with reference to the accompanying drawings, in which.

DETAILED DESCRIPTION

Figure 1:
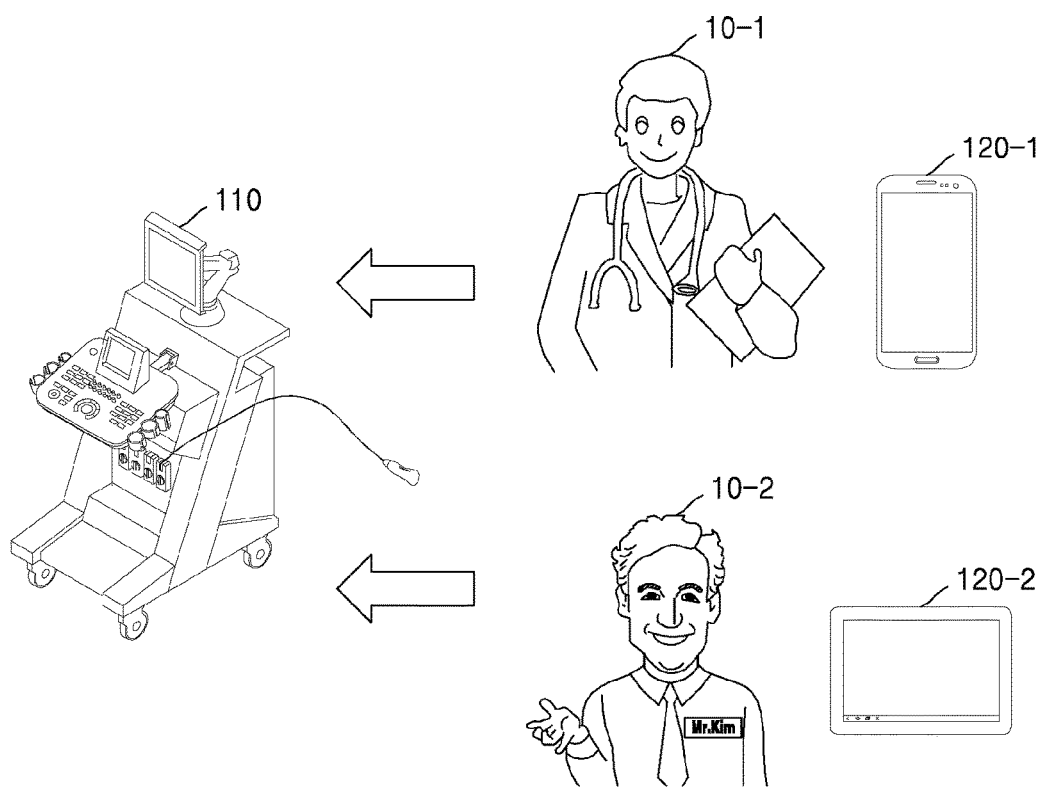
FIG. 1 is a schematic conceptual diagram of a method of detecting a user within a short distance from a device, performed by the device, according to one or more exemplary embodiments.

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments may be practiced without those specifically defined matters. Also, well-known functions or constructions may not be described in detail because they would obscure the description with unnecessary detail.

In the present specification, "configuration information" refers to information that indicates conditions related to operations of a device, for example, displaying a user interface or capturing images. The "configuration information" may also include information indicating conditions related to operations of devices.

For example, when the device is a medical imaging apparatus, configuration information may include setting values (i.e., setting values related to a user interface), date format, time settings, indexes to be displayed via a viewer, functions to be included in a tool bar and displayed via the viewer, addresses (e.g., URLs) of remote services, display formats of the addresses of the remote control tools, and display formats of names of imaging targets. The date format may refer to a setting value that indicates how to display the current date. The time settings may refer to a setting value about the current time that is to be set in the device. Types of the indexes to be displayed via the viewer may include types of indexes to be displayed among setting values or estimated values (e.g., in a case of an X-ray imaging apparatus, doses and exposure indexes) that are set in the device. The functions to be included in the tool bar may refer to a list of function buttons that are frequently used by the user among functions of the device, for example, drawing a circle, drawing a quadrilateral, inputting text, and a virtual ruler.

As another example, in a case that the device is a medical imaging apparatus (e.g., an X-ray imaging apparatus), configuration information may include setting values related to capturing images (i.e., conditions related to operations of the device), for example, a setting value related to automatic deleting of images, whether to automatically confirm images, whether to automatically transmit images, whether to use auto exposure control (AEC), whether to store an original image, and whether to estimate a dose-area product (DAP). The setting value related to automatic deleting of images may indicate setting whether to automatically delete images in the device and setting a ratio between all images to images to be deleted. Whether to automatically confirm images may indicate setting whether to automatically store captured images without confirmation of the user. Whether to automatically transmit images may indicate setting whether to automatically transmit captured images to another device, for example, a picture archiving and communication system (PACS). Whether to use AEC may indicate setting whether to apply the AEC when capturing images. Whether to store the original image may indicate setting whether to store an original captured image. Whether to estimate the DAP may indicate setting whether to estimate the DAP when capturing images.

Also, "user configuration information" may indicate configuration information that is determined by the user to use the device.

Also, in the specification, a "medical imaging apparatus" may include not only an apparatus for capturing medical images, for example, an X-ray imaging apparatus, a tomography apparatus, a magnetic resonance imaging (MRI) apparatus, and an ultrasound imaging apparatus, but also a system for storing, reading, and searching for medical image information, for example, PACS.

Also, in the present specification, a "mobile device" may include, but is not limited to a mobile phone, a smartphone, a tablet personal computer (PC), a personal digital assistant (PDA), a handheld personal communication system (PCS), or a navigation device.

Also, when a "device" is a medical imaging apparatus in the present specification, a "user" may be, but is not limited to, a medical expert, such as a medical doctor, a nurse, a medical laboratory technologist, or a technician who repairs a medical apparatus.

Also, in the present specification, a "user interface" may indicate an apparatus for interacting with a user, software for interacting with a user, or a combination thereof. For example, when a device is an X-ray imaging apparatus, a user interface may include, but is not limited to, values related to capturing images such as Kvp, mA, mSec, or mAs, or a tool bar for manipulating the X-ray imaging apparatus.

FIG. 1 is a schematic conceptual diagram of a method of detecting a user within a short distance from a device 110, performed by the device 110, according to one or more exemplary embodiments.

Referring to FIG. 1, users 10-1 and 10-2 may use a device 110. To determine whether the user 10-1 or the user 10-2 is within a short distance from the device 110, the device 110 may detect that a mobile device 120-1 of the user 10-1 or a mobile device 120-2 of the user 10-2 is within the short distance. The device 110 may register identification (ID) information about the mobile devices 120-1 and 120-2 to detect the mobile devices 120-1 and 120-2. The registering the ID information about the mobile devices 120-1 and 120-2 includes storing the ID information in the device 110. The ID information about the mobile devices 120-1 and 120-2 may include at least one selected from user ID information and device ID information. The user ID information may include information for identifying the users 10-1 and 10-2, such as a user ID and a password. The device ID information may include information for identifying the mobile devices 120-1 and 120-2, such as a MAC address or a device unique identifier (DUID).

According to one or more exemplary embodiments, the device 110 may determine a distance between the device 110 and each of the mobile devices 120-1 and 120-2 to determine whether the mobile devices 120-1 and 120-2 are within the short distance from the device 110. The device 110 may determine that the distance between the device 110 and each of the mobile devices 120-1 and 120-2 may vary depending on exemplary embodiments. For example, the device 110 may determine the distance between the device 110 and each the mobile devices 120-1 and 120-2 based on strength of short distance wireless communication signals or low frequency acoustic signals from the mobile devices 120-1 and 120-2. Alternatively, according to one or more exemplary embodiments, the mobile devices 120-1 and 120-2 may determine the distance between the device 110 and each of the mobile devices 120-1 and 120-2.

The range of "short distance" may vary depending on exemplary embodiments. For example, "short distance" may refer to a distance of about 10 m in which Bluetooth communication is possible, or a distance determined by users in one or more cases.

Examples of short distance communication techniques may include, but are not limited to, wireless LAN, Wi-Fi, Bluetooth, ZigBee, Wi-Fi Direct (WFD), ultra-wideband (UWB), Infrared Data Association (IrDA), Bluetooth low energy (BLE), and Near Field Communication (NFC).

Figure 2:
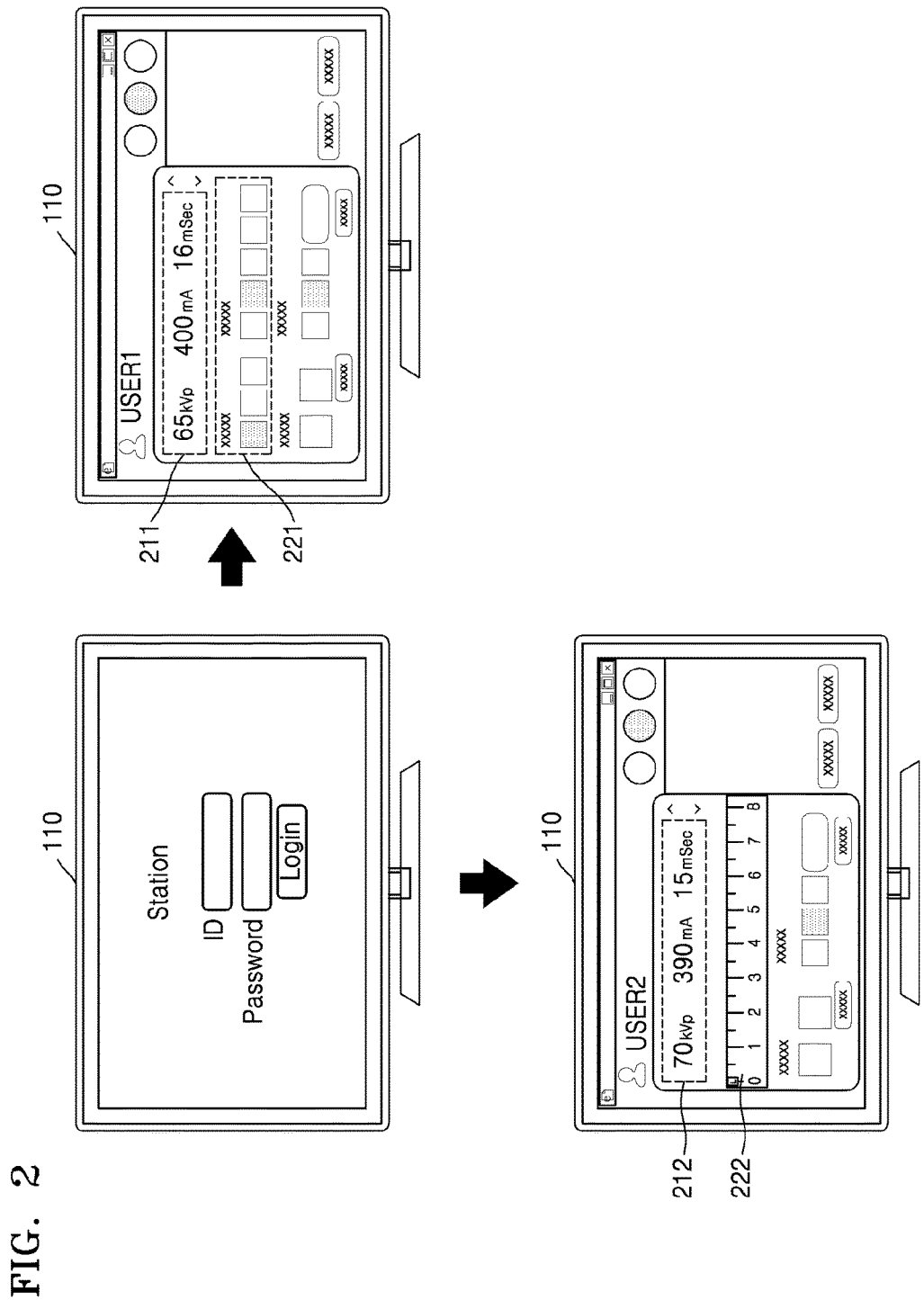
FIG. 2 is a schematic conceptual diagram of a method of displaying a setting value according to users and a user interface, performed by a device, according to one or more exemplary embodiments.

FIG. 2 is a schematic conceptual diagram of a method of displaying a setting value according to users and a user interface, performed by the device 110, according to one or more exemplary embodiments.

Referring to FIG. 2, when the device 110 detects the mobile device 120-1 within a short distance, the device 110 may be set based on user configuration information that is set by the user 10-1. Also, the device 110 may display a setting value 211 or a user interface 221 based on the user configuration information.

Alternatively, when the device 110 detects the mobile device 120-2 within a short distance, the device 110 may be set based on user configuration information that is set by the user 10-2. Also, the device 110 may display a setting value 212 or a user interface 222 based on the user configuration information.

Figure 3:
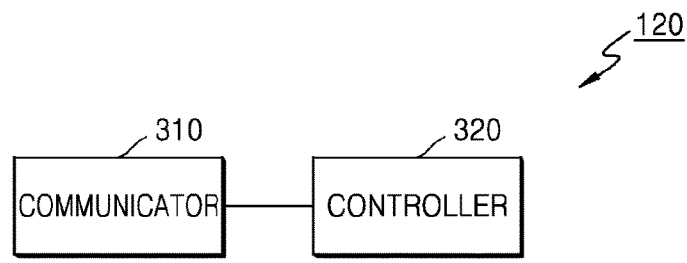
FIG. 3 is a schematic block diagram of a mobile device according to one or more exemplary embodiments.

FIG. 3 is a schematic block diagram of a mobile device 120 according to one or more exemplary embodiments. FIG. 3 is for describing one or more exemplary embodiments, and the mobile device 120 may include more or less elements than those shown in FIG. 3. Also, the elements shown in FIG. 3 may be replaced with other similar elements according to exemplary embodiments.

According to one or more exemplary embodiments, the mobile device 120 includes a communicator 310 and a controller 320.

When the mobile device 120 is within a short distance from the device 110, the communicator 310 according to one or more exemplary embodiments receives a configuration information request from the device 110. According to exemplary embodiments, the communicator 310 may directly communicate with the device 110 via short distance wireless communication technology or via a network in which the device 110 and the mobile device 120 are connected to each other.

According to one or more exemplary embodiments, the communicator 310 may repeatedly transmit short distance wireless communication signals that may be received by the device 110. For example, the communicator 310 may include a short distance communication interface that may repeatedly transmit short distance wireless communication signals based on the BLE protocol. The device 110 may receive the short distance wireless communication signals from the communicator 310, and the device 110 may determine a distance between the device 110 and the mobile device 120 based on a received signal strength indicator (RSSI). According to other exemplary embodiments, the communicator 310 may receive signals from the device 110, and the controller 320 may determine a distance between the device 110 and the mobile device 120 based on the received signals.

The controller 320 according to one or more exemplary embodiments may control each element of the mobile device 120. When the communicator 310 receives the configuration information request from the device 110, the controller 320 controls the communicator 310 such that the communicator 310 transmits user configuration information stored in the mobile device 120 to the device 110. The user configuration information may be stored in, but is not limited to, a storage medium in the device 110 or a cloud server connected with the device 110. Also, according to one or more exemplary embodiments, the communicator 310 may further transmit ID information of the mobile device 120 to the device 110 under the control of the controller 320.

Figure 4:
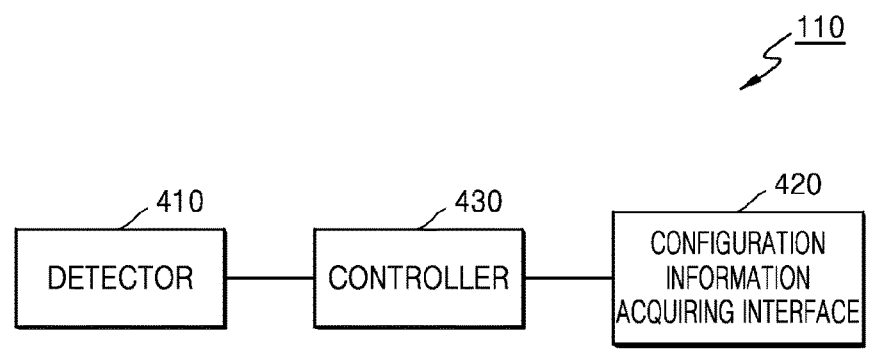
FIG. 4 is a block diagram of a device according to one or more exemplary embodiments.

FIG. 4 is a block diagram of the device 110 according to one or more exemplary embodiments. FIG. 4 is for describing one or more exemplary embodiments, and the device 110 may include more or less elements than those shown in FIG. 4. Also, the elements shown in FIG. 4 may be replaced with other similar elements according to exemplary embodiments.

According to one or more exemplary embodiments, the device 110 includes a detector 410, a configuration information acquiring interface 420, and a controller 430.

The detector 410 may detect the mobile device 120 that is located within a short distance. According to one or more exemplary embodiments, the detector 410 may determine a distance between the device 110 and the mobile device 120, and when the determined distance is the same as or less than a predetermined value, the detector 410 may determine that the mobile device 120 is within a short distance. For example, the detector 410 may include a receiver (e.g., Bluetooth dongle) for receiving signals from the mobile device 120. As the distance between the mobile device 120 and the device 110 increases, the strength of the received signals due to signal attenuation decreases, and thus, the detector 410 may determine the distance based on the strength of the received signals. According to other exemplary embodiments, the distance between the mobile device 120 and the device 110 may be determined by the controller 430. However, exemplary embodiments are not limited thereto. The distance between the mobile device 120 and the device 110 may be determined by using various methods according to exemplary embodiments.

According to one or more exemplary embodiment, the configuration information acquiring interface 420 acquires, from the mobile device 120 within a short distance from the device 110, user configuration information that is stored in the mobile device 120. For example, the configuration information acquiring interface 420 may transmit a configuration information request to the mobile device 120 via short distance wireless communication technology. The configuration information acquiring interface 420 may receive the user configuration information from the mobile device 120 in response to the request. Also, according to one or more exemplary embodiments, the detector 410 and the configuration information acquiring interface 420 may be implemented as a single element by using a short distance wireless communication interface.

Also, the controller 430 may control each element of the device 110. Also, the controller 430 controls the device 110 such that an operation of the device 110 is performed based on the user configuration information from the configuration information acquiring interface 420. For example, the controller 430 may control the device 110 such that the device 110 displays a user interface that is configured based on the acquired user configuration information. As another example, when the device 110 is a medical imaging apparatus, the device 110 may capture and store medical images according to the acquired user configuration information.

Figure 5:
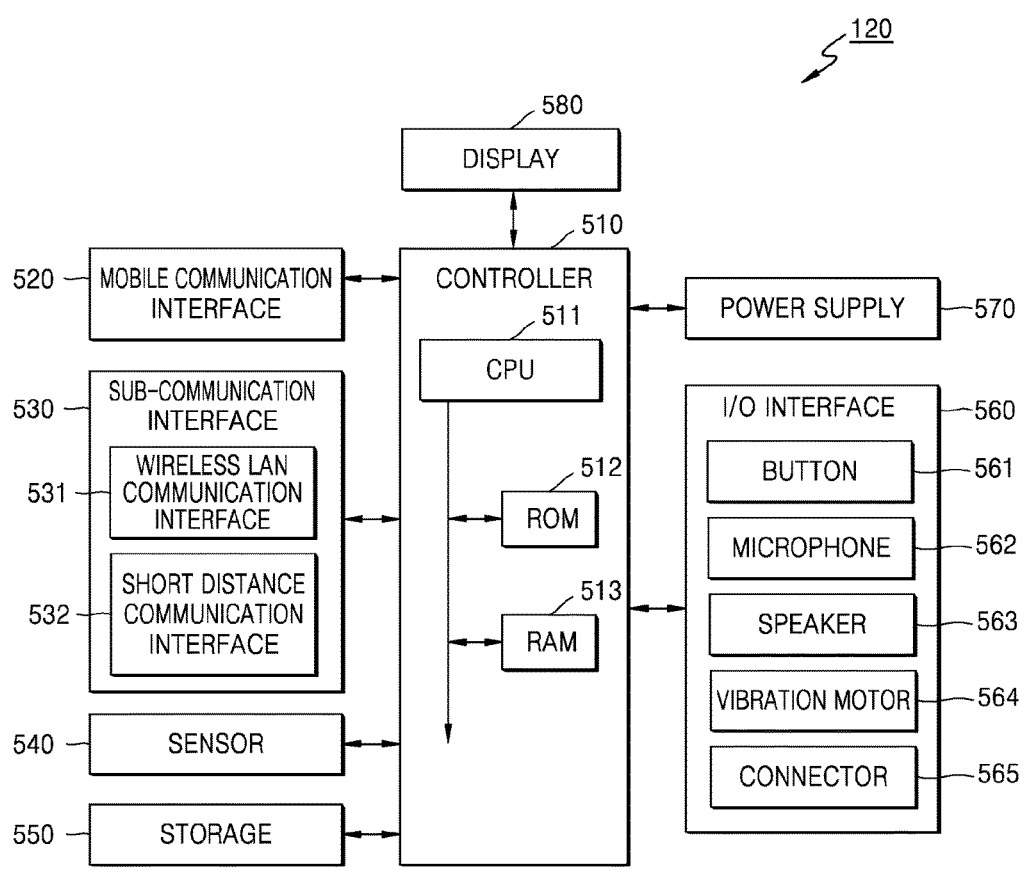
FIG. 5 is a detailed block diagram of a mobile device according to one or more exemplary embodiments.

FIG. 5 is a detailed block diagram of the mobile device 120 according to one or more exemplary embodiments. FIG. 5 is for describing one or more exemplary embodiments, and the mobile device 120 may include more or less elements than those shown in FIG. 5. Also, the elements shown in FIG. 5 may be replaced with other similar elements according to exemplary embodiments.

The mobile device 120 according to one or more exemplary embodiments may be connected with an external device by using a mobile communication interface 520, a sub-communication interface 530, and a connector 565. The external device may include the device 110.

Referring to FIG. 5, the mobile device 120 includes a controller 510, the mobile communication interface 520, the sub-communication interface 530, a sensor 540, a storage 550, an input/output (I/O) interface 560, a power supply 570, and a display 580. The sub-communication interface 530 includes a wireless LAN communication interface 531 and a short distance communication interface 532. The I/O interface 560 includes a button 561, a microphone 562, a speaker 563, a vibration motor 564, and the connector 565.

The controller 510 includes a central processing unit (CPU) 511, ROM 512 that stores a control program for controlling the mobile device 120, and RAM 513 that stores signals or data that is input from outside the mobile device 120 or functions as a memory space for operations performed by the mobile device 120. The CPU 511 may include a plurality of processors such as a single-core, dual-core, triple-core, or quad-core processor. The CPU 511, the ROM 512, and the RAM 513 may be connected to each other via an internal bus.

The controller 510 controls the mobile communication interface 520, the sub-communication interface 530, the sensor 540, the storage 550, the I/O interface 560, the power supply 570, and the display 580.

The controller 510 may control the mobile communication interface 520 such that the mobile communication interface 520 uses at least one antenna and performs mobile communication so that the mobile device 120 is connected with an external device. The mobile communication interface 520 may transmit and receive wireless signals for voice calls, video calls, and transmissions of short messages or multimedia messages with a cellular phone of which a contact number is input to the mobile device 120, a smartphone, a tablet PC, or other devices.

According to one or more exemplary embodiments, the sub-communication interface 530 may include only the wireless LAN communication interface 531, or only the short distance communication interface 532.

The controller 510 may control the wireless LAN communication interface 531 such that the wireless LAN communication interface 531 is connected with the Internet at a place where a wireless access point (AP) is provided. The wireless LAN communication interface 531 may support the wireless LAN standard IEEE 802.11x of the Institute of Electrical and Electronics Engineers (IEEE). The controller 510 may control the short distance communication interface 532 such that the short distance communication interface 532 performs a short distance wireless communication between the mobile device 120 and the device 110. Examples of the short distance wireless communication techniques may include Bluetooth, IrDA, ZigBee, and Wi-Fi direct.

The sensor 540 may include at least one sensor that detects a status of the mobile device 120 or a status of surroundings of the mobile device 120. For example, the sensor 540 may include a proximity sensor that detects whether an object is near the mobile device 120, an illumination sensor that detects the amount of light around the mobile device 120, or a motion sensor that detects motions (e.g., rotations or acceleration of the mobile device 120, or vibration applied to the mobile device 120) of the mobile device 120. More or less sensors may be included in the sensor 540 according to the performance of the mobile device 120.

The controller 510 may control the storage 550 such that the storage 550 stores data with respect to operations of the mobile communication interface 520, the sub-communication interface 530, the I/O interface 560, and the sensor 540. The storage 550 may store a control program for controlling the mobile device 120 or the controller 510, and applications. Also, the, storage 550 may store user configuration information for setting the device 110 with respect to the user of the mobile device 120.

The term "storage" may include the storage 550, the ROM 512 and the RAM 513 in the controller 510 or a memory card inserted into the mobile device 120. The storage may include a non-volatile memory, a volatile memory, a hard disk drive (HDD), or a solid state drive (SSD).

According to one or more exemplary embodiments, the I/O interface 560 may include at least one selected from the button 561, the microphone 562, the speaker 563, the vibration motor 564, and the connector 565.

The button 561 may be formed at a front surface, a side surface, or a back surface of a housing of the mobile device 120, and may include at least one selected from a power/lock button, a volume button, a menu button, a home button, a back button, and a search button.

The controller 510 may control the microphone 562 such that the microphone 562 receives voice or sounds and generates electric signals.

The controller 510 may control the speaker 563 such that the speaker 563 output sounds with respect to various signals to the outside of the mobile device 120. The speaker 563 may output a sound that corresponds to a function performed by the mobile device 120. The speaker 563 may be formed at an appropriate location or locations on the housing of the mobile device 120.

The controller 510 may control the vibration motor 564 such that the vibration motor 564 changes electric signals to mechanical vibrations. For example, the vibration motor 564 may operate when the mobile device 120 that is in a vibration mode receives a voice call from another device.

The connector 565 may be used as an interface for connecting an external device or a power source with the mobile device 120. Under the control of the controller 510, data stored in the storage 550 of the mobile device 120 may be transmitted to an external device or data may be received from the external device via a cable connected to the connector 565. Power may be input from the power source or a battery may be charged via the cable connected to the connector 565.

The controller 510 may control the power supply 570 such that the power supply 570 supplies power to at least one battery that is located in the housing of the mobile device 120. Also, the power supply 570 may supply power that is input from an external power source to elements in the mobile device 120 via the cable connected to the connector 565.

The display 580 may output various user interfaces. For example, the display 580 may output a user interface for the user to determine user configuration information. According to one or more exemplary embodiments, the display 580 may include a touch screen. In the exemplary embodiments, a touch input is not limited to an input that is transmitted when a portion of the body of the user or a touch input tool contacts the touch screen. The touch input may include a non-contact input (e.g., a distance between the touch screen and the portion of the body is the same as or less than 1 mm). The touch screen may be, for example, a resistive type, a capacitive type, an infrared type, or an ultrasound wave type.

According to one or more exemplary embodiments, the communicator 310 of FIG. 3 may be configured by using at least one selected from the mobile communication interface 520, the sub-communication interface 530, and the I/O interface 560 of FIG. 5.

Figure 6:
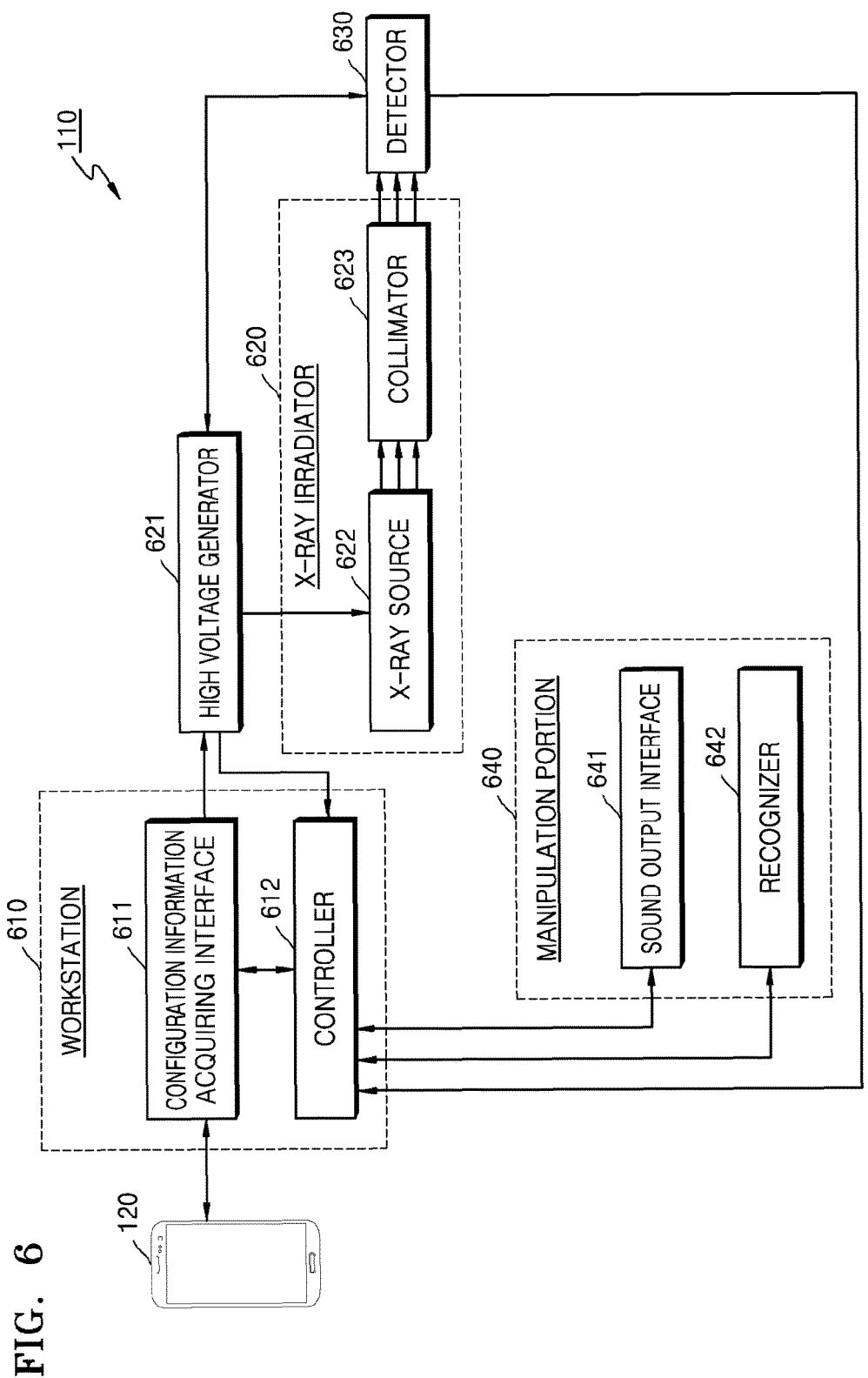
FIG. 6 is a detailed block diagram of a device according to one or more exemplary embodiments.

FIG. 6 is a detailed block diagram of the device 110 according to one or more exemplary embodiments. FIG. 6 is a block diagram of the device 110 when the device 110 is an X-ray imaging apparatus. Although the block diagram illustrates only an example in which the device 110 is an X-ray imaging apparatus, the device 110 may be a medical imaging apparatus other than the X-ray imaging apparatus, for example, a tomography apparatus, an MRI apparatus, and an ultrasound imaging apparatus. Alternatively, the device 110 may be a computing apparatus other than a medical imaging apparatus, for example, a PC and a laptop.

A workstation 610 may include an input interface to which a user may input an instruction for manipulating the device 110, a configuration information acquiring interface 611 that acquires configuration information for setting the device 110, and a controller 612 that controls overall operations of the device 110.

Based on the configuration information that is acquired by the configuration information acquiring interface 611, a high voltage generator 621 generates a high voltage for generating X-rays, and applies the high voltage to an X-ray source 622.

An X-ray irradiator 620 includes the X-ray source 622 that receives the high voltage generated by the high voltage generator 621 and generates X-rays, and a collimator 623 that guides the X-rays that are generated from the X-ray source 622.

A detector 630 detects X-rays that are irradiated onto an object from the X-ray irradiator 620.

Also, the device 110 includes a sound output interface 641 that is controlled by the controller 612 such that the sound output interface 641 outputs sounds that indicate imaging-related information, for example, X-ray irradiation. The device 110 also includes a recognizer 642 that recognizes whether the mobile device 120 is within a short distance from the device 110. Respective locations of the recognizer 642 and the configuration information acquiring interface 611 may vary depending on exemplary embodiments. For example, although FIG. 6 illustrates that the recognizer 642 is included in a manipulation portion 640, alternatively, the recognizer 642 may be included in the workstation 610.

The workstation 610, the X-ray irradiator 620, the high voltage generator 621, and the detector 630 may be wired or wirelessly connected to each other. When the workstation 610, the X-ray irradiator 620, the high voltage generator 621, and the detector 630 are wirelessly connected, a synchronizer for synchronizing clocks between each element may be further included in the device 110.

The input interface may include a keyboard, a mouse, a touch screen, an audio recognizer, a fingerprint recognizer, an iris recognizer, and any other input interface that is well-known to one of ordinary skill in the art. The user may input an instruction for X-ray irradiation via the input interface. In this case, the input interface may include a switch for inputting the instruction. The switch may be provided such that the switch has to be pressed twice to input an X-ray irradiation instruction. When the user manipulates the switch, the input interface may generate signals that correspond to an instruction that is input by the manipulation of the switch, i.e., a preparation signal and an irradiation signal, and output the signals to the high voltage generator 621 that generates a high voltage.

The controller 612 may control respective locations of the X-ray irradiator 620 and the detector 630, capture timing, and an imaging condition according to an imaging condition included in the user configuration information acquired by the configuration information acquiring interface 611. The controller 612 controls the high voltage generator 621 and the detector 630 according to the configuration information, X-ray irradiation timing, X-ray strength, and an X-ray irradiation area. Also, according to the imaging condition, the controller 612 may adjust a location of the detector 630 and control an operation timing of the detector 630.

Also, the controller 612 may generate a medical image of an object by using image data that is received from the detector 630. The controller 612 may receive image data from the detector 630, remove noise of the image data, adjust dynamic ranges, perform interleaving operation, and thus generate a medical image of the object.

Figure 7:
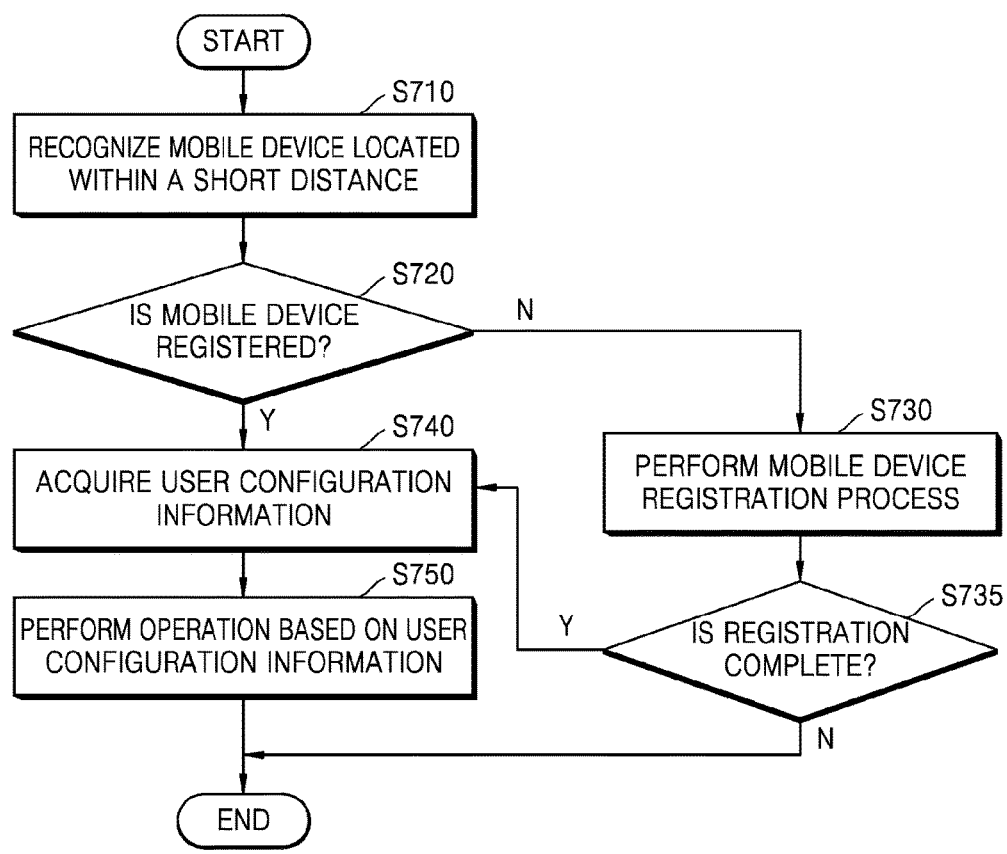
FIG. 7 is a flowchart of a process of controlling a device, according to one or more exemplary embodiments.

FIG. 7 is a flowchart of a process of controlling the device 110, according to one or more exemplary embodiments.

In operation S710, the device 110 recognizes a mobile device that is located within a short distance, by using the detector 410. The mobile device 120 within the short distance may be detected with various methods according to exemplary embodiments. For example, the device 110 may use sound waves or strength of signals received from the mobile device 120 to estimate a distance between the device 110 and the mobile device 120. When a distance between the device 110 and the mobile device 120 is the same as or less than a predetermined value based on the strength of the signals received from the mobile device 120, the device 110 may determine that the mobile device 120 is within the short distance. Also, when the mobile device 120 broadcasts wireless communication signals (e.g., BLE signals) that include device ID information for identifying the mobile device 120, the device 110 may recognize the mobile device 120 based on the received wireless communication signals. Also, to transmit and receive more pieces of data, the device 110 may connect wireless communication services according to another communication technique (e.g., WFD) with the mobile device 120, by using a communication interface in the configuration information acquiring interface 420.

In operation S720, the device 110 determines whether the detected mobile device 120 is registered in the device 110. For example, the device 110 may compare the device ID information received in operation S710 with device ID information that is stored in the device 110. When one of the pieces of device ID information stored in the device 110 corresponds to the device ID information received in operation S710, the device 110 may determine that the mobile device 120 is registered in the device 110. If the device 110 determines that the detected mobile device 120 is not registered in the device 110, the device 110 continues in operation S730. Otherwise, the device 110 continues in operation S740.

In operation S730, the device 110 performs a mobile device registration process. The mobile device registration process is a process for registering the mobile device 120 to the device 110. To register the mobile device 120 to the device 110, the device 110 may output a user interface for selecting whether to register the detected mobile device 120. For example, FIG. 9 is a diagram of a user interface that displays a list related to the detected mobile device 120.

Figure 9:
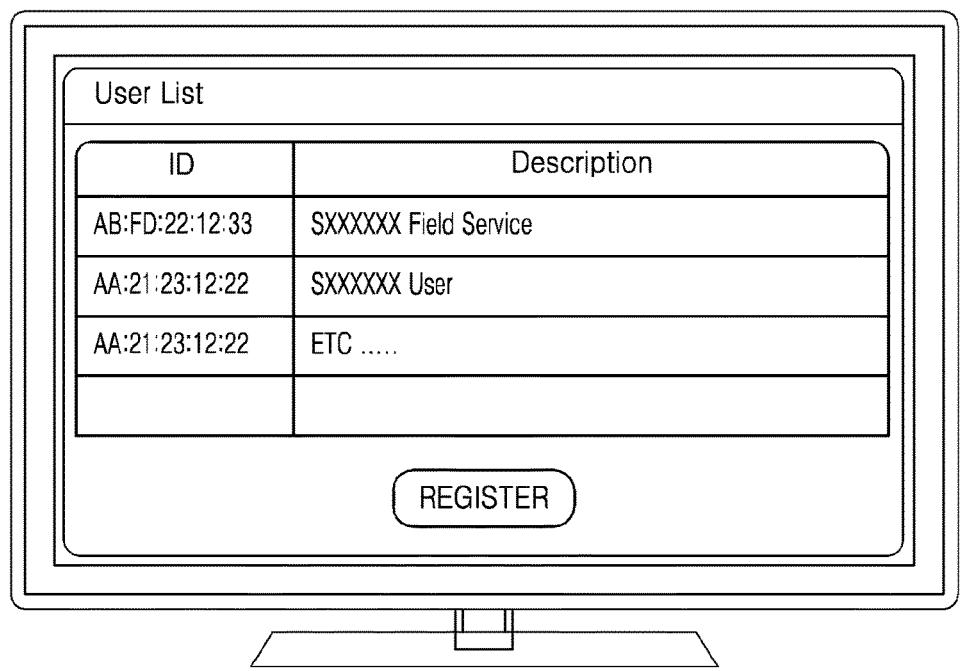
FIG. 9 is a diagram of a user interface for registering a mobile device that is displayed on a device, according to one or more exemplary embodiments.

FIG. 9 is a diagram of a user interface for registering the mobile device 120 that is displayed on the device 110, according to one or more exemplary embodiments. Referring to FIG. 9, the user may select the mobile device 120 to register from the list related to the mobile device 120, and register the selected mobile device 120 to the device 110 by pressing a 'Register' button. To register the mobile device 120, the device 110 may acquire ID information of the mobile device 120, which includes at least one selected from device ID information and user ID information, from the mobile device 120. The device 110 may register the mobile device 120 to the device 110 by storing the acquired ID information. The device 110 may transmit a registration request to the mobile device 120 to acquire the ID information related to the mobile device 120.

In operation S735, the device 110 determines whether the mobile device registration process is complete, i.e., whether the mobile device 120 is registered to the device 110. If the device 110 determines that the mobile device registration is complete, the device 110 continues in operation S740. Otherwise, the process ends.

In operation S740, the device 110 acquires user configuration information from the mobile device 120. For example, the device 110 may acquire the user configuration information from the mobile device 120 via short distance wireless communication (e.g., Bluetooth or WFD). In this case, the device 110 may transmit a request for the user configuration information to the mobile device 120. Alternatively, when a signal is received from the mobile device 120 in operation S710, the device 110 may register the mobile device 120 by using ID information included in the received signal. However, exemplary embodiments are not limited thereto. The user configuration information may be not stored in the device 110.

In operation S750, the device 110 performs an operation based on the acquired user configuration information. Operations of the device 110 may include all operations that may be performed by the device 110. For example, based on the user configuration information, the device 110 may determine user interface elements (e.g., a tool bar) to be included in a user interface or information (e.g., an indicator related to imaging when the device 110 is a medical device) to be displayed via the user interface. The device 110 may output a user interface that is configured based on the user configuration information. Alternatively, when the device 110 is a medical imaging apparatus that may capture medical images, the device 110 may set an imaging condition for capturing medical images based on the user configuration information. The user configuration information may include at least one setting value for capturing medical images. The at least one setting value may include at least one selected from a dose, an exposure index, Kvp, mA, mSec, mAs, AEC, density, a size of a focal spot, a collimator correction value, physical resolution of the detector 630, and logical resolution of the detector 630.

The device 110 may transmit image information that is related to an image stored in the device 110 to the mobile device 120. In this case, the device 110 may be a medical imaging apparatus. The image information may include, for example, at least one selected from a distance between an object and the X-ray source 622 when the stored image was captured, a dose, an exposure index, Kvp set in the device 110, mA set in the device 110, mSec set in the device 110, mAs set in the device 110, estimated Kvp, AEC, density, a size of a focal spot, a collimator correction value, temperature of the detector 630, sensitivity of the detector 630, physical resolution of the detector 630, logical resolution of the detector 630, a deviation index, spatial resolution, detector calibration time, captured portion, image capture number, and a retake rate (a rejection rate). The 'captured portion' refers to information that indicates which object is captured in an image. The 'image capture number' may refer to information that indicates the total number of image-capturing performed by the device 110 or the number of image-capturing performed by the user of the mobile device 120 using the device 110. The 'retake rate' may refer to a rate of images that are not successfully captured and have to be captured again. Because information such as the 'retake rate' is provided to the mobile device 120, the user of the mobile device 120 may determine whether a setting value according to the user configuration information related to the mobile device 120 is effective for capturing images.

Figure 8:
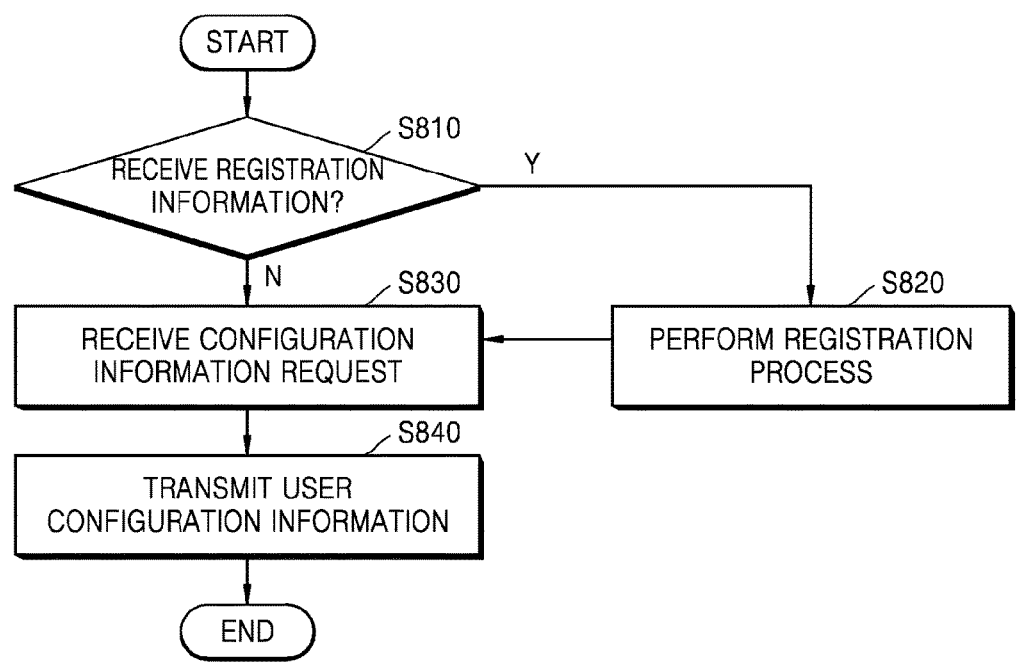
FIG. 8 is a flowchart of a process of controlling a mobile device, according to one or more exemplary embodiments.

FIG. 8 is a flowchart of a process of controlling the mobile device 120 according to one or more exemplary embodiments.

In operation S810, the mobile device 120 determines whether a registration request or information is received from the device 110. If the mobile device 120 determines that the registration request or information is received, the mobile device 120 continues in operation S820. Otherwise, the mobile device 120 continues in operation S830.

In operation S820, the mobile device 120 performs a registration process. For example, the mobile device 120 may transmit information related to the mobile device 120 to the device 110, so that the mobile device 120 may be registered to the device 110.

According to other exemplary embodiments, the mobile device 120 may repeatedly transmit short distance wireless communication signals that include device ID information for identifying the mobile device 120. In this case, operations S810 and S820 may be omitted because the device 110 may register the mobile device 120 based on the transmitted short distance wireless communication signals.

In operation S830, the mobile device 120 receives a configuration information request from the device 110.

In operation S840, the mobile device 120 transmits user configuration information that is stored in the mobile device 120 to the device 110.

According to other exemplary embodiments, the mobile device 120 may receive image information that is related to an image stored in the device 110, from the device 110. The image information may include, for example, at least one selected from a distance between an object and the X-ray source 622 when the stored image was captured, a dose, an exposure index, Kvp set in the device 110, mA set in the device 110, mSec set in the device 110, mAs set in the device 110, estimated Kvp, AEC, density, a size of a focal spot, a collimator correction value, temperature of the detector 630, sensitivity of the detector 630, physical resolution of the detector 630, logical resolution of the detector 630, a deviation index, spatial resolution, detector calibration time, captured portion, image capture number, and a retake rate (a rejection rate). The mobile device 120 may display the received image information via the display 580 so that the user of the mobile device 120 may check the image information related to the image stored in the device 110.

Figure 10:
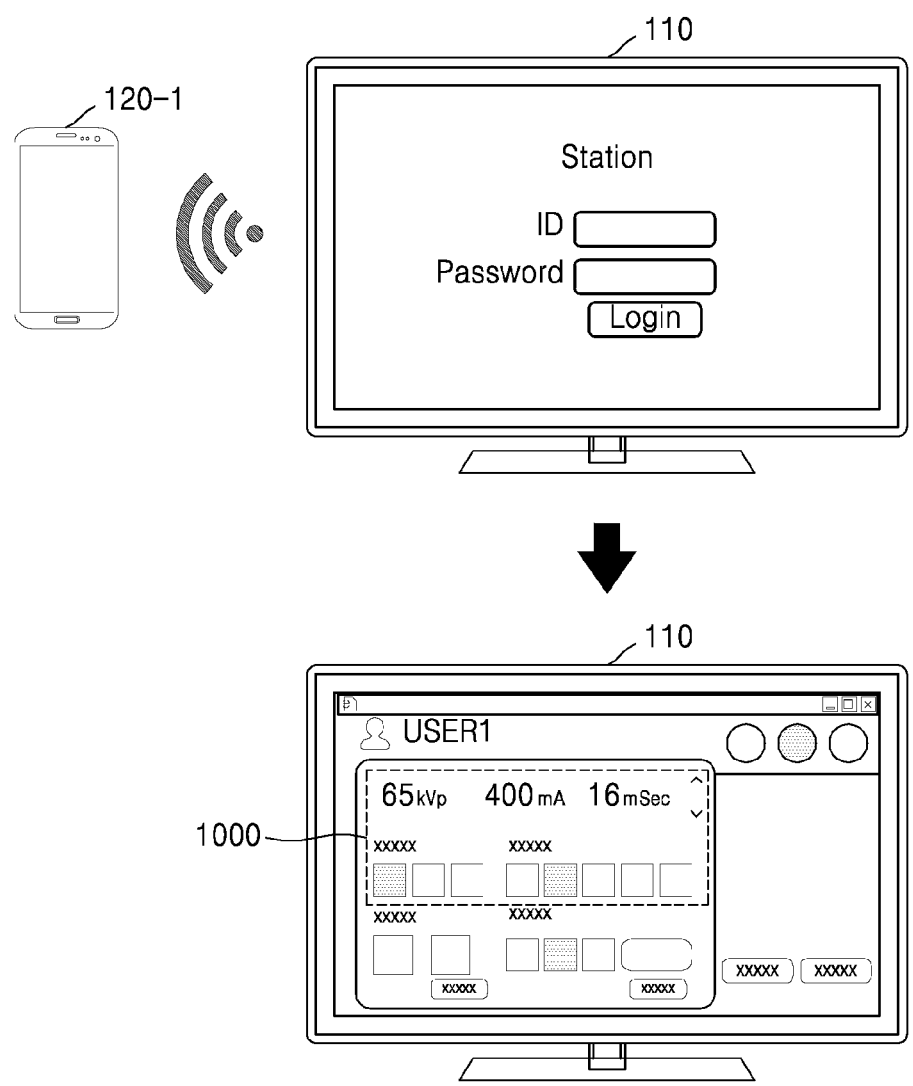
FIGS. 10 and 11 are diagrams of operations of a device when one mobile device or at least two mobile devices are detected, according to one or more exemplary embodiments.
Figure 11:
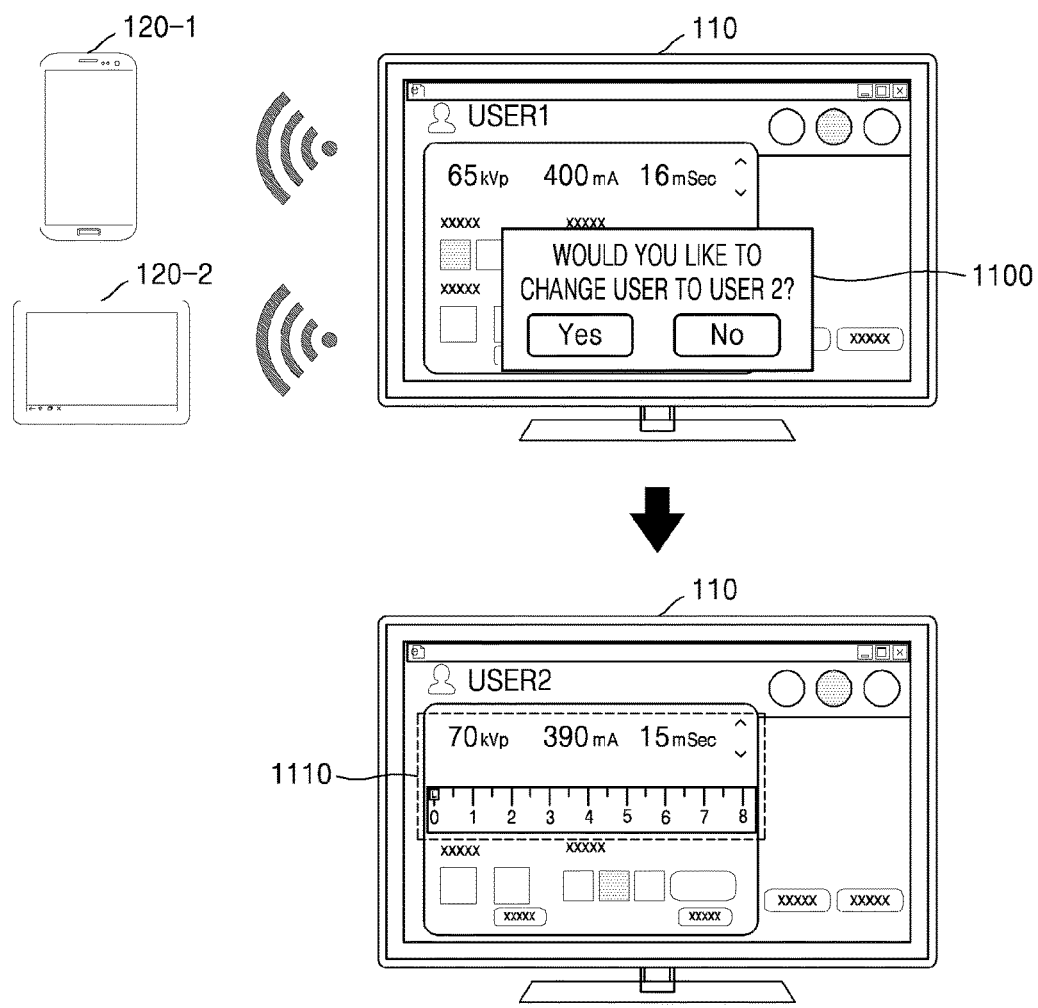

FIGS. 10 and 11 are diagrams of operations of the device 110 when one mobile device or at least two mobile devices are detected, according to one or more exemplary embodiments.

Referring to FIG. 10, when only one mobile device, i.e., the first mobile device 120-1, is near the device 110, the device 110 receives user configuration information from the first mobile device 120-1, and sets an operation condition of the device 110 based on the received user configuration information. For example, the device 110 displays a user interface 1000 that is configured according to a condition that is set by a user of the first mobile device 120-1. That is, the device 110 may be set to a state in which the user of the first mobile device 120-1 logs onto the device 110 by inputting his or her ID and password.

Another mobile device may approach the device 110 while the device 110 is set based on the user configuration information that is received from the first mobile device 120-1. Referring to FIG. 11, the first mobile device 120-1 and a second mobile device 120-2 are located near the device 110. In this case, the device 110 determines whether to change settings of the device 110 according to user configuration information that is stored in the second mobile device 120-2. A method of determining whether to change the settings of the device 110 may vary depending on exemplary embodiments. For example, the device 110 may set a grade of a user for each registered mobile device. When a user of the second mobile device 120-2 has a higher grade than the user of the first mobile device 120-1, the device 110 may acquire user configuration information from the second mobile device 120-2 and change the settings of the device 110. As another example, when the second mobile device 120-2 is detected, the device 110 may output the user interface 1100 for selecting whether to change the settings of the device 110. The user may select whether to change the settings of the device 110 via the user interface 1100.

When the settings of the device 110 are changed according to user configuration information that is stored in the second mobile device 120-2, the device 110 acquires the user configuration information from the second mobile device 120-2. The device 110 changes the settings of the device 110 based on the user configuration information that is received from the second mobile device 120-2. For example, as shown in FIG. 11, the device 110 displays a user interface 1110 that is configured based on the user configuration information received from the second mobile device 120-2.

While not restricted thereto, an exemplary embodiment can be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an exemplary embodiment may be written as a computer program transmitted over a computer-readable transmission medium, such as a carrier wave, and received and implemented in general-use or special-purpose digital computers that execute the programs. Moreover, it is understood that in exemplary embodiments, one or more of the above-described elements can include circuitry, a processor, a microprocessor, etc., and may execute a computer program stored in a computer-readable medium.

The foregoing exemplary embodiments and advantages are merely exemplary and are not to be construed as limiting. The present teaching may be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A method of controlling a device, the method comprising:

detecting, by the device, a mobile device within a distance from the device;

receiving, by the device, a setting value of a user interface to be displayed by the device, from the detected mobile device;

displaying, by the device, the user interface, based on the setting value received from the detected mobile device;

detecting, by the device, another mobile device within the distance from the device;

determining, by the device, whether to change the setting value received from the mobile device to another setting value of the user interface to be displayed by the device and to be received from the other mobile device, based on at least one among a grade of each of the mobile device and the other mobile device and an input selection of the other mobile device; and receiving, by the device, the other setting value of the user interface to be displayed by the device, from the other mobile device, in response to the determining to change the setting value to the other setting value.

2. The method of claim 1, further comprising determining whether the mobile device is registered to the device,
wherein the receiving comprises receiving the setting value from the mobile device in response to the determining that the mobile device is registered to the device.

3. The method of claim 2, further comprising registering the mobile device to the device in response to the determining that the mobile device is not registered to the device.

4. The method of claim 1, further comprising receiving a wireless signal from the mobile device,
wherein the detecting comprises detecting that the mobile device is within the distance from the device, based on the wireless signal.

5. The method of claim 1, wherein the device comprises a medical imaging apparatus.

6. The method of claim 5, further comprising:
receiving, by the device, one or more setting values for capturing an image, from the detected mobile device; and
capturing, by the device, an image, based on the one or more setting values received from the detected mobile device.

7. The method of claim 5, further comprising transmitting, to the mobile device, information of an image.

8. The method of claim 7, wherein the information of the image comprises an image retake rate.

9. A non-transitory computer-readable storage medium storing a program comprising instructions configured to cause a computer to perform the method of claim 1.

10. A method of providing configuration information to a device, the method being performed by a mobile device, and the method comprising:
receiving, by the mobile device, a configuration information request from the device in response to the mobile device being within a distance from the device; and
transmitting, by the mobile device, a setting value of a user interface to be displayed by the device, to the device, in response to the receiving the configuration information request, the setting value being used by the device to display the user interface,
wherein the device:
displays the user interface, based on the setting value transmitted by the mobile device;
detects another mobile device within the distance from the device;
determines whether to change the setting value transmitted by the mobile device to another setting value of the user interface to be displayed by the device and to be received from the other mobile device, based on at least one among a grade of each of the mobile device and the other mobile device and an in input selection of the other mobile device; and
receives the other setting value of the user interface to be displayed by the device, from the other mobile device, in response to the determining to change the setting value to the other setting value.

11. The method of claim 10, further comprising:
receiving a registration request from the device; and
transmitting, to the device, identification information of the mobile device in response to the receiving the registration request.

12. The method of claim 10, further comprising transmitting, to the device, a communication signal.

13. The method of claim 10, wherein the device comprises a medical imaging apparatus.

14. The method of claim 13, further comprising transmitting, by the mobile device, one or more setting values for capturing an image, to the device, in response to the receiving the configuration information request, the one or more setting values being used by the device to capture an image.

15. The method of claim 13, further comprising:
receiving information of an image from the device; and
displaying at least one among the information of the image and statistics of the information of the image.

16. The method of claim 15, wherein the information of the image comprises an image retake rate.

17. A non-transitory computer-readable storage medium storing a program comprising instructions configured to cause a computer to perform the method of claim 10.

18. A device comprising:
a detector configured to detect a mobile device within a distance from the device;
an interface configured to receive, from the detected mobile device, a setting value of a user interface to be displayed by the device; and
a controller configured to control a display to display the user interface, based on the setting value received from the detected mobile device,
wherein the detector is further configured to detect another mobile device within the distance from the device,
the controller is further configured to determine whether to change the setting value received from the mobile device to another setting value of the user interface to be displayed by the device and to be received from the other mobile device, based on at least one among a grade of each of the mobile device and the other mobile device and an input selection of the other mobile device, and
the interface is further configured to receive the other setting value of the user interface to be displayed by the device, from the other mobile device in response to the controller determining to change the setting value to the other setting value.

19. The device of claim 18, wherein the device comprises a medical imaging apparatus.

20. The device of claim 19, wherein the interface is further configured to receive, from the detected mobile device, one or more setting values for capturing an image, and
the controller is further configured to control the device to capture an image, based on the one or more setting values received from the detected mobile device.

21. The device of claim 19, wherein the interface is further configured to transmit, to the mobile device, information of an image.

22. The device of claim 18, wherein the controller is further configured to determine whether the mobile device is registered to the device, and
the interface is further configured to:
transmit, to the mobile device, a registration request in response to the controller determining that the mobile device is not registered in the device; and
receive identification information of the mobile device from the mobile device.

23. A device comprising:
a detector configured to detect a mobile device within a distance from the device;
an interface configured to receive user configuration information from the mobile device; and
a controller configured to perform an operation of the device, based on the user configuration information,
wherein the detector is further configured to detect another mobile device within the distance from the device,
the controller is further configured to determine whether to change the user configuration information received from the mobile device to other user configuration information to be received from the other mobile device, based on at least one among a grade of each of the mobile device and the other mobile device and an input selection of the other mobile device, and
the interface is further configured to receive the other user configuration information from the other mobile device in response to the controller determining to change the user configuration information to the other user configuration information.

24. The device of claim 18, wherein the interface is further configured to transmit, to the mobile device, a configuration information request for the setting value.

25. A mobile device comprising:
a communicator configured to receive a configuration information request from a device in response to the mobile device being within a distance from the device; and
a controller configured to control the communicator to transmit, to the device, a setting value of a user interface to be displayed by the device, in response to the communicator receiving the configuration information request, the setting value being used by the device to display the user interface,
wherein the device:
displays the user interface, based on the setting value transmitted by the mobile device;
detects another mobile device within the distance from the device;
determines whether to change the setting value transmitted by the mobile device to another setting value of the user interface to be displayed by the device and to be received from the other mobile device, based on at least one among a grade of each of the mobile device and the other mobile device and an input selection of the other mobile device; and
receives the other setting value of the user interface to be displayed by the device, from the other mobile device, in response to the determining to change the setting value to the other setting value.

26. The mobile device of claim 25, wherein the device comprises a medical imaging apparatus.

27. The mobile device of claim 26, wherein the controller is further configured to control the communicator to transmit, to the device, one or more setting values for capturing an image, in response to the communicator receiving the configuration information request, the one or more setting values being used by the device to capture an image.

28. The mobile device of claim 26, further comprising a display,
wherein the communicator is further configured to receive information of an image from the device, and
the controller is further configured to control the display to display at least one among the information of the image and statistics of the information of the image.

* * * * *